United States Patent
Freilich et al.

(10) Patent No.: US 8,137,103 B1
(45) Date of Patent: Mar. 20, 2012

(54) IMPLANT SYSTEM

(75) Inventors: Martin A. Freilich, West Hartford, CT (US); Jacqueline P. Duncan, Granby, CT (US); A. Jon Goldberg, West Hartford, CT (US); Charles J. Burstone, Farmington, CT (US)

(73) Assignee: University of Connecticut, Farmington, CT (US)

(*) Notice: Subject to any disclaimer, the term of this patent is extended or adjusted under 35 U.S.C. 154(b) by 0 days.

(21) Appl. No.: 09/311,464

(22) Filed: May 13, 1999

(51) Int. Cl.
*A61C 3/00* (2006.01)
(52) U.S. Cl. .................. 433/172; 433/173; 433/215
(58) Field of Classification Search .................. 433/172, 433/173, 174, 175, 176, 213, 214
See application file for complete search history.

(56) References Cited

U.S. PATENT DOCUMENTS

| | | | |
|---|---|---|---|
| 3,066,112 A | 11/1962 | Bowen | |
| 3,179,623 A | 4/1965 | Bowen | |
| 3,194,784 A | 7/1965 | Bowen | |
| 3,715,331 A | 2/1973 | Molnar | |
| 3,751,399 A | 8/1973 | Lee | |
| 3,926,906 A | 12/1975 | Lee | |
| 4,544,359 A | 10/1985 | Waknine | |
| 4,547,531 A | 10/1985 | Waknine | |
| 4,708,654 A * | 11/1987 | Branemark | 433/213 |
| 4,717,341 A | 1/1988 | Goldberg | |
| 4,894,012 A | 1/1990 | Goldberg | |
| 4,906,191 A * | 3/1990 | Soderberg | 433/214 |
| 4,955,811 A * | 9/1990 | Lazzara et al. | 433/213 X |
| 4,988,298 A * | 1/1991 | Lazzara et al. | 433/173 |
| 5,052,929 A * | 10/1991 | Seal | 433/173 |
| 5,064,374 A * | 11/1991 | Lundgren | 433/173 |
| 5,125,841 A * | 6/1992 | Carlsson et al. | 433/213 |
| 5,276,068 A | 1/1994 | Waknine | |
| 5,427,906 A * | 6/1995 | Hansen | 433/173 |
| 5,444,104 A | 8/1995 | Waknine | |
| 5,662,475 A * | 9/1997 | Mena | 433/172 |
| 5,684,103 A | 11/1997 | Jia | |
| 5,782,918 A * | 7/1998 | Klardie et al. | 606/60 |
| 5,810,590 A * | 9/1998 | Fried et al. | 433/172 |
| 5,823,776 A * | 10/1998 | Duerr et al. | 433/173 |
| 5,994,246 A | 11/1999 | Denry | |
| 6,013,694 A | 1/2000 | Jia | |
| 6,030,209 A | 2/2000 | Panzera | |

(Continued)

FOREIGN PATENT DOCUMENTS

DE 40 15 008 A1 11/1991
WO WO 94/01488 7/1994

OTHER PUBLICATIONS

Cambridge Dictionaries Online—Cambridge University Press 2004.

(Continued)

*Primary Examiner* — Nicholas D Lucchesi
(74) *Attorney, Agent, or Firm* — McCarter & English, LLP

(57) ABSTRACT

An implant system may comprise implants, abutments, cylinders and a structural framework with a veneer thereon. A prosthesis comprises the structural framework and veneer. The cylinders are provided with grooves or shelves thereon to retain a structural framework thereon. The structural framework may comprise fiber reinforced composite material which is disposed on and around the cylinders to provide the framework for a prosthesis. Abutments are provided for single or small implant systems wherein the abutments comprise mechanical retentive features such as grooves, holes, nodules or beads thereon for retaining polymeric material thereon.

13 Claims, 7 Drawing Sheets

U.S. PATENT DOCUMENTS

| | | | |
|---|---|---|---|
| 6,056,547 A * | 5/2000 | Names | 433/173 |
| 6,086,662 A | 7/2000 | Brodkin | |
| 6,087,282 A | 7/2000 | Panzera | |
| 6,103,383 A | 8/2000 | Prasad | |

OTHER PUBLICATIONS

Merriam-Webster Online Dictionary 2004.
yourDictionary.com—American Heritage Dictionary 1996-2002.
PCT International Search Report, Sep. 12, 2000.
Freilich, Martin, A., DDS, et al, "The Design and Fabrication of Fiber-Reinforced Implant Prostheses" Oct. 2002, The Journal of Prosthetidc Dentistry.
Freilich, Martin A., DDS, et al "Clinical Evaluation of Fiber-Reinforced Fixed Bridges" Nov. 2002, JADA, vol. 133.
Ruyter IE; Ekstrand K; Bjork N, "Development of Carbon/graphite fiber reinforced poly(methyl methacrylate) suitable for implant-fixed dental bridges." Dental Materials, 1986 2 (1): 6-9, February.
Bjork N; Ekstrand K; Ruyter E, "Carbon/graphite fiber reinforced polymer implant bridge prostheses." Swedish Dental Journal, 1985 2S :77-84.
Bjork N; Ekstrand K, Ruyter I.E., "Carbon/graphite fibre reinforced poly(methyl methacrylate)." Biomaterials, 1986 vol. 7 January 73-75.
Meiers, J.C., Freilich, M.A., "Chairside prefabricated fiber-reinforced resin composite fixed partial dentures." Quintessence International, vol. 32, No. 2, 2001.
Bergendal T; Ekstrand K; Karlsson U., "Evaluation of Implant Supported Carbon/Graphite Fiberinforced poly methyl methacrylate prostheses." Clinical Oral lmplans Research 1995: 6:246-253.
Bjork N; Ekstrand K; Ruyter IE., Implant-fixed dental bridges from carbon/graphite fibre reinforced poly methyl methacrylate). Biomaterials 1986 7 (1): 73-5 Jan.

* cited by examiner

IMPLANT SYSTEM

TECHNICAL FIELD

The present invention relates generally to implant systems and more specifically to implant systems having fiber-reinforced composite components.

BACKGROUND OF THE INVENTION

Dental implants are routinely used to replace missing teeth in both the maxilla and mandible jawbones. These implants are restored with crowns and/or bridges. The choice and design depend upon the number of teeth missing and the location of the implants. The single crown typically consists of a metal framework veneered with porcelain. Smaller bridges are also made from metal and porcelain while the larger prostheses consist of a metal framework or substructure and an acrylic resin denture tooth supra-structure. For crowns and all bridges, the metal framework incorporates machined gold alloy components called cylinders. The cylinders allow the metal framework to be connected to the abutments which are in turn connected to the implants. The periodontal ligament is a soft tissue membrane located in the mouth between tooth and bone and absorbs energy during the chewing process. Dental implants are fused to bone and, as noted above, are typically fabricated of a metal superstructure which lacks resilience characteristic of the periodontal ligament. This results in higher stresses to implants and the dental prosthesis. Further, the metal framework is cast and does not typically fit onto the abutments well. Thus, it must often be cut and refitted and the pieces are then soldered together. The process is time consuming and the materials used to fabricate the framework and abutments (e.g., gold) can be expensive. Additionally, it may be difficult to completely cover the metal framework which results in a less aesthetic appearance.

Carbon/graphite reinforced autopolymerizing poly(methyl methacrylate) bridges and frameworks were attempted heretofore but were found insufficient due to the procedures and designs used to fabricate the bridges and frameworks. Retention of the materials was found inadequate and fractures were found to occur in the final prosthesis. Bergendal et al., 1995 Clin Oral Imp Res, reported limited success in a clinical trial using carbon/graphite fiber reinforced PMMA for the fabrication of a framework in an implant system. Fractures occurred in the framework adjacent the end abutment propagating through the acrylic resin and carbon/graphite fibers to the gold and/or titanium cylinders. The cylinders were not designed to provide adequate retention of the framework materials. Additionally, fracture sites in connection with cylinders showed incomplete wetting of the fibers with polymer.

It is desirable to provide an implant system which is able to provide adequate retention of fiber reinforced composite material and to reduce and/or prevent fracture of the prostheses made therefrom. It is advantageous to provide an implant system having good esthetics and adaptability.

SUMMARY OF THE INVENTION

These and other objects and advantages are accomplished by the implant system herein. The system may include implants, abutments, cylinders and a structural framework with a veneer thereon. A prosthesis comprises the structural framework and veneer.

In accordance with one embodiment herein, cylinders are provided with grooves or shelves thereon to retain a structural framework thereon. The structural framework may comprise fiber reinforced composite material which is disposed on and around the cylinders to provide the framework for a prosthesis.

In accordance with another embodiment herein, abutments are provided for single or small implant systems wherein the abutments comprise mechanical retentive features such as grooves, holes, nodules or beads on the surface for retaining polymeric material thereon.

The implant system herein provides an aesthetic and adaptable system having adequate retention of fiber reinforced composite material and good fracture toughness.

BRIEF DESCRIPTION OF THE DRAWINGS

Features of the present invention are disclosed in the accompanying drawings, wherein similar reference characters denote similar elements throughout the several views, and wherein.

DETAILED DESCRIPTION OF THE INVENTION

Figure 1:
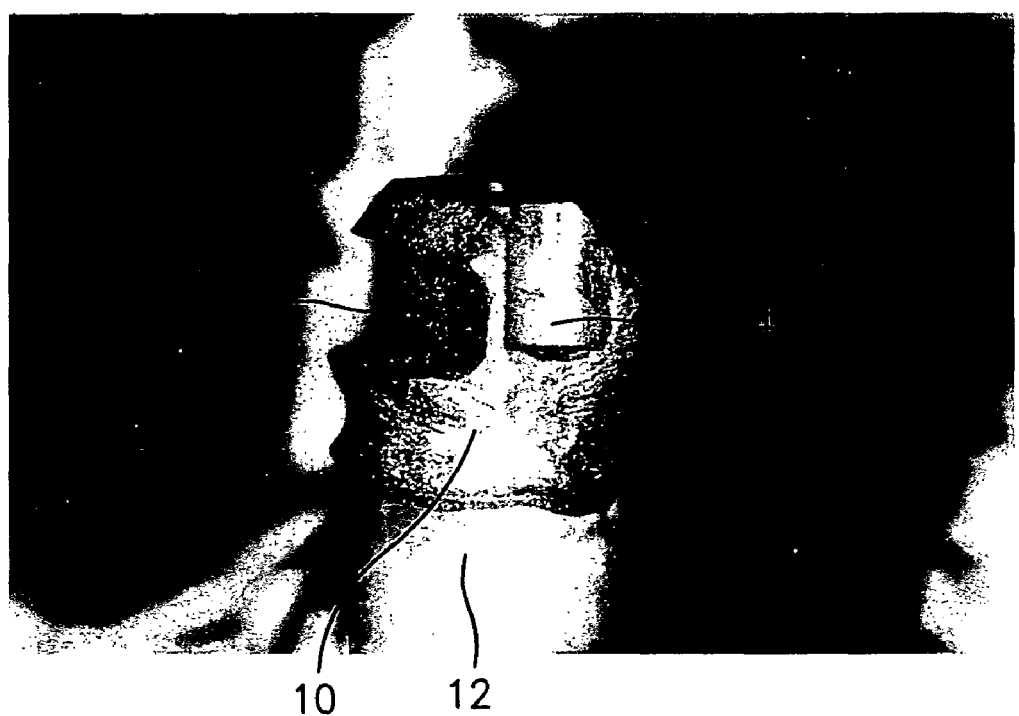
FIG. 1 is a perspective view of a cylinder of an implant system of the invention.
Figure 2:
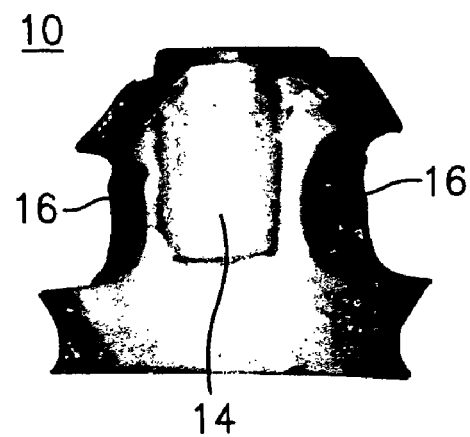
FIG. 2 is a perspective view of the cylinder of FIG. 1 showing a proximal surface thereof.

The implant system of the invention may comprise implants, abutments, cylinders and a framework to support the implant crown or superstructure of the prosthesis. The implant system may be a single implant crown, a small prosthesis for replacing one or a few teeth or a large prosthesis for replacing all or a large number of teeth. Implants are implanted into the patient's jawbone. The abutments typically act as connectors between the implants and the cylinders which include a framework and upon completion, a prosthesis. Cylinders fit onto the abutments and are connected or attached thereto by known means, preferably by a screw or like component or by a luting material known in the industry such as Lute-It® composite, available from Jeneric/Pentron Inc., Wallingford, Conn. Attention is directed to FIGS. 1 and 2 which depict a cylinder 10. In FIG. 1, cylinder 10 is positioned on an abutment analog 12 on a stone cast 13 (in FIG. 4) which is similar to an actual abutment which is eventually connected to the implant in the mouth.

Figure 3:
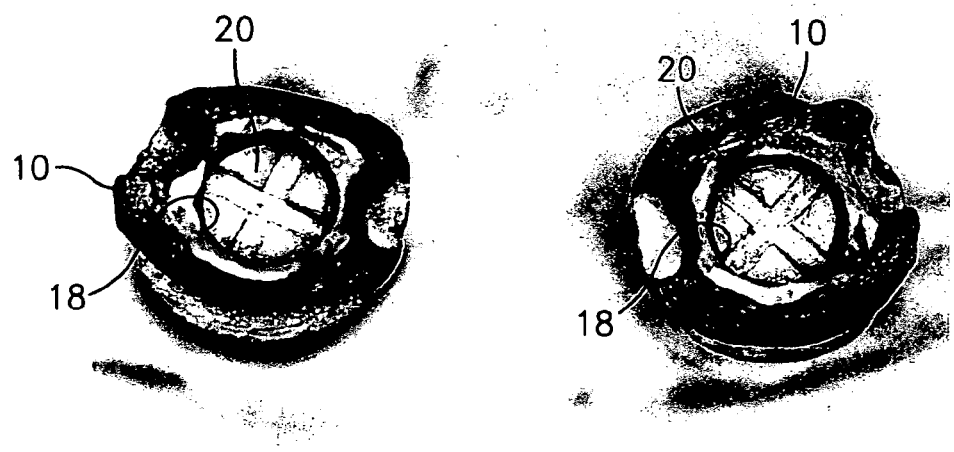
FIG. 3 is a top plan view of cylinders of the invention having screws therein.

Cylinder 10 is designed to orient and retain a structural framework material, or a composite or ceramic material thereon for single crowns and small prostheses. Preferably, the structural framework material is a fiber reinforced composite material. Retaining grooves or shelves may be disposed anywhere on cylinders 10 to retain and hold the structural framework or other material thereon. Preferably, the grooves or shelves are disposed vertically, as depicted in FIGS. 1 and 2 at 14, and are preferably located on the proximal surfaces of cylinders 10. As shown in the Figures, these retaining grooves have at least two sides to allow appropriate positioning of the fiber reinforced composite framework between cylinders and mechanically retain the framework in place. Alternatively, or in addition to grooves 14, horizontal grooves or shelves 16 may be provided on cylinders 10 and are preferably located on the facial and lingual surfaces of the cylinders and assist in controlling the fiber reinforced composite while it is wrapped around the cylinders to complete the framework. Horizontal grooves 16 are shown having two sides, a top side and a bottom side, while vertical grooves 14 are shown having three sides, a left side, a right side and a bottom side. Additionally, nodules, beads or holes may be disposed on the surface of the cylinders to aid in the retention of polymeric material. Preferably, the nodules and the like are of a size smaller than the shelves or grooves and can also be located on the entire surface of the cylinders including the shelves and grooves or on a portion of the surface of the cylinders. FIG. 3 shows cylinders 10 with bores or screw holes 18 extending axially through cylinders 10. Screws 20 are shown inserted in screw holes 18 and extend through to abutment analogs 12 shown in FIG. 4. Screws 20 connect and retain cylinders 10 to abutment analogs 12 on cast 13 or eventually to abutments in the mouth.

Figures 5A, 5B, 5C:
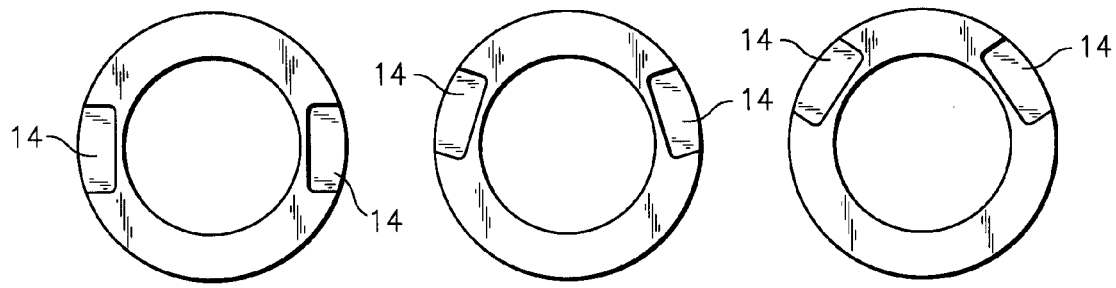
FIG. 5 is a top plan view of cylinders showing variations in the locations of grooves thereon.

Cylinders 10 may be fabricated of any known material such as metal, plastic, ceramic, polymeric material and mixtures thereof. Vertical grooves 14 may be located at a variety of different angles depending on where the cylinders are positioned within the framework. FIG. 5 shows a top plan view of three different positions of grooves 14. FIG. 5A shows grooves 14 disposed directly across from one another at the 3 and 9 o'clock positions. FIG. 5B shows grooves 14 located slightly upward with respect to the position of grooves 14 in FIG. 5A between the 2 and 3 o'clock positions and between the 9 and 10 o'clock positions. FIG. 3 shows grooves 14 located at the 2 and 10 o'clock positions.

Figure 6:
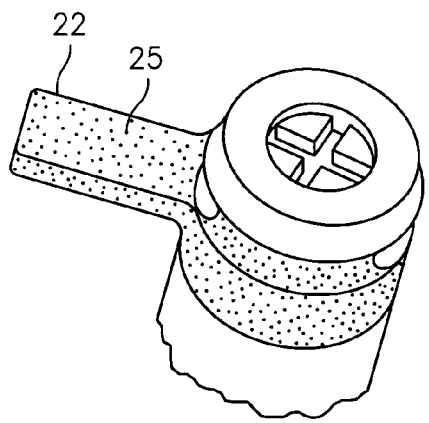
FIG. 6 is a perspective view of a terminal cylinder of the implant system.
Figure 7:
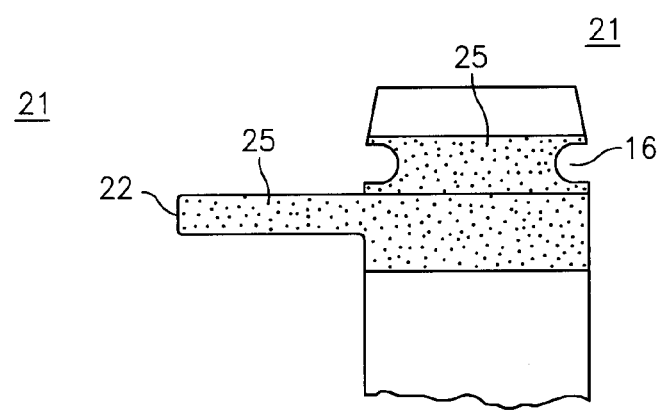
FIG. 7 is a side view of FIG. 6.

FIGS. 6 and 7 show a terminal cylinder 21 having a cantilever support 22 located on one side of cylinder 21. The support 22 provides reinforcement to the ends 23 of the framework 26 shown in FIGS. 8 and 9. Cylinder 10 as well as cylinder 21 may include beads, nodules, holes or the like to aid in the retention of polymeric material thereon. FIGS. 6 and 7 show nodules 25 on support 22 and grooves 16.

Figure 10:
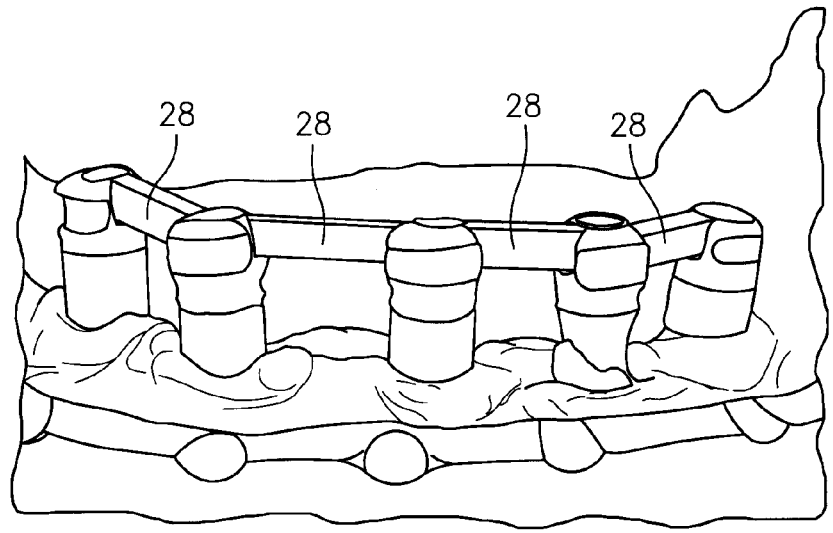
FIG. 10 is a perspective view of the framework of FIGS. 8 and 9 partially complete.
Figure 8:
FIG. 8 is a perspective view showing the cylinders of FIG. 4 having a framework thereon.
Figure 9:
FIG. 9 is a top plan view of the framework and cylinders of FIG. 8.
Figure 11:
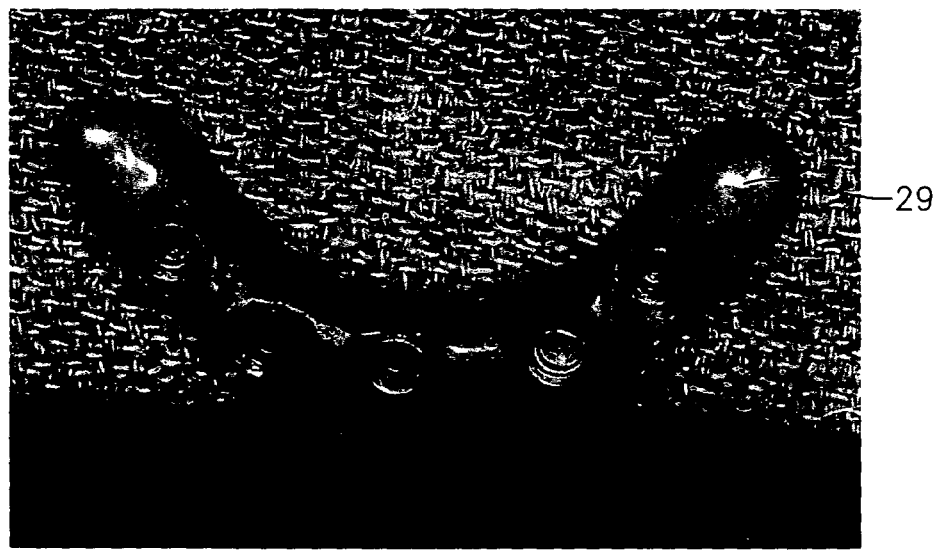
FIG. 11 is a bottom view of a finished prosthesis.

FIGS. 8 and 9 show fiber reinforced composite material 24 deposited between, on and around cylinders 10 to form a framework 26. Grooves 14 and 16 assist in retaining fiber reinforced composite material 24 on cylinders 10. Retaining grooves 14 and 16 allow appropriate positioning of fiber reinforced composite framework 26 between and around cylinders 10 and mechanically hold framework 26 in place. Fiber reinforced material 24 may be in the form of strips, ribbon or like form for fabrication of framework 26. Preferably, fiber reinforced material 24 is in the form of bars or rods 28 as shown in FIG. 10 which may be placed into grooves 14 between cylinders 10 and on cantilever supports 22 on terminal or end cylinders 21. Rods 28 may be partially or fully cured prior to placement in grooves 14. Thereafter, uncured or partially cured fiber reinforced composite material 24 is preferably wrapped around the cylinders fitting within grooves 16 for retention and cured to form framework 26. A prosthesis is then fabricated on the fiber reinforced composite framework. Preferably, a material which mimics the pink connective tissue in the mouth is used to cover framework 26 and provide the base or lower portion of the prosthesis. Denture base materials such as poly(methyl methacrylate), resin composites such as Sculpture® composite available from Jeneric/Pentron Inc, Wallingford, Conn. and similar materials can be used to form the base of the prosthesis. FIG. 11 shows a base 29 of denture base material which is applied over framework 26 to form the understructure of the prosthesis. Teeth are placed or fabricated on the occlusal surface of the prosthesis as shown at 32 in FIGS. 12 and 13.

Figure 12:
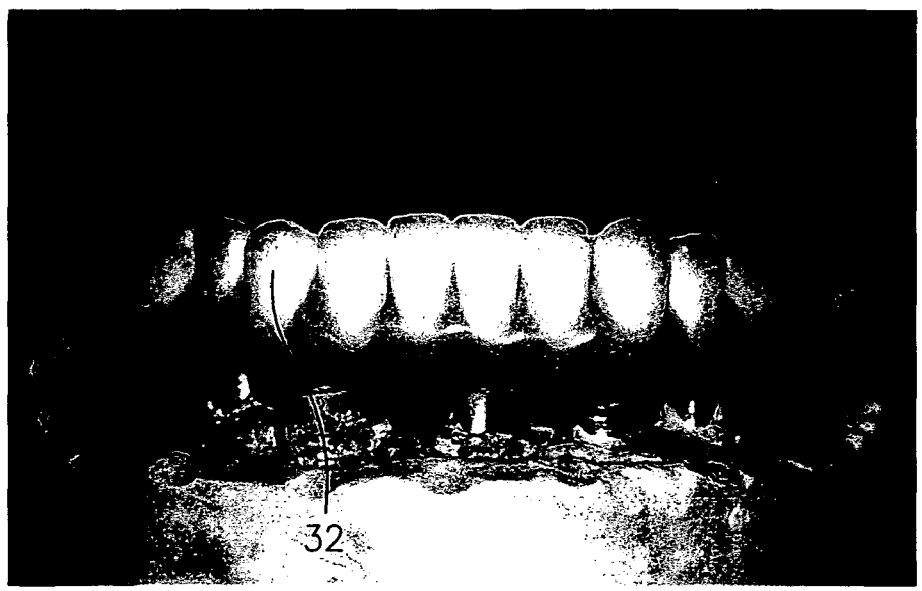
FIG. 12 is a perspective view of the prosthesis of FIG. 11.
Figure 13:
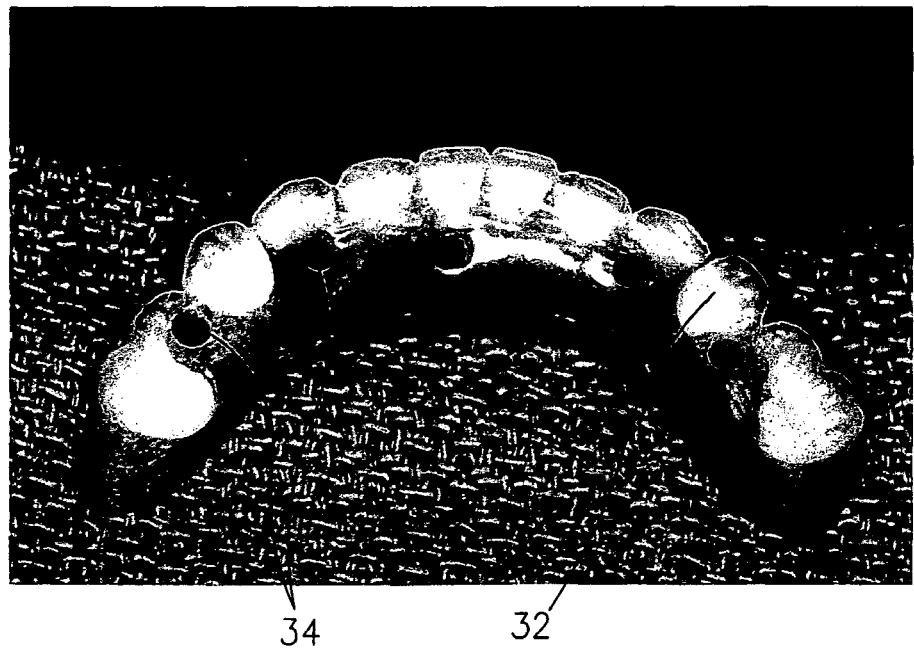
FIG. 13 is a top perspective view of the prosthesis in FIG. 11 showing bores or screw holes therein.

FIGS. 12 and 13 show prosthesis 30 with teeth 32. FIG. 13 shows bores 34 which extend through prosthesis 30 and receive retaining members such as screws or the like for retention of prosthesis 30 into the patient's mouth. The prosthesis is placed in the patient's mouth and screws or the like are inserted into bore 34 and through to and into abutments which are connected to implants located in the patient's jawbone.

Figure 4:
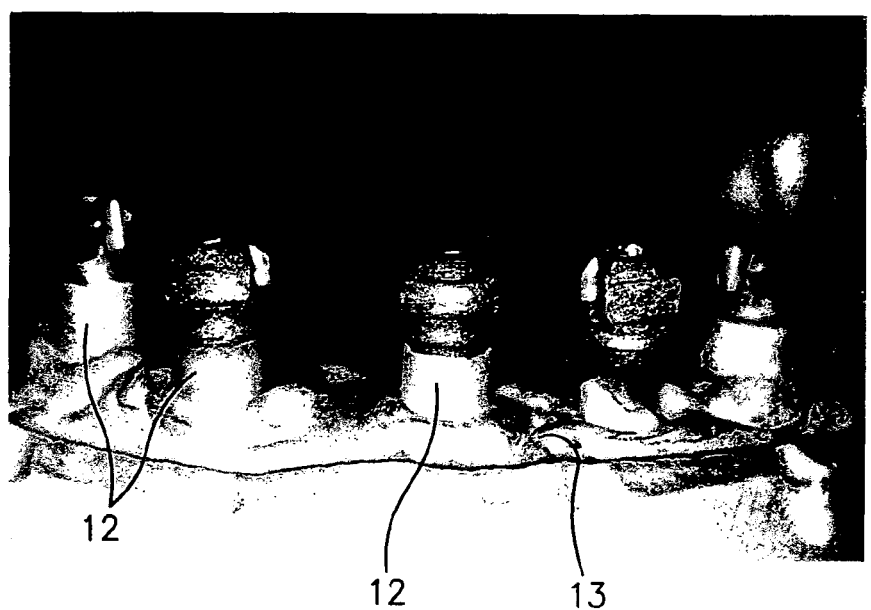
FIG. 4 is a perspective view of a series of cylinders attached to corresponding abutment analogs.

In accordance with the method of manufacture of the implant assembly herein, a series of cylinders are placed on analog abutments 12 as shown in FIG. 4. A structural framework is built on the series of cylinders using a fiber-reinforced composite or like material. Preferably, fiber reinforced composite rods or bars are prefabricated and placed between the proximal shelves 14. Thereafter, fiber reinforced composite material may be wrapped around the series of cylinders and retained in facial and lingual grooves 16. Preferably, the fiber reinforced composite material is uncured or only partially cured and is wrapped around the cylinders a plurality of times to provide integrity to the framework. A bonding material such as FibreKor® Special Resin or Flow-It® resin, both available from Jeneric/Pentron Inc., Wallingford, Conn. may be applied between layers of the fiber reinforced composite material to aid in retention and adherence thereof. The layers may be cured before the application of additional layers or may be cured after completion of the framework. A denture base material may be applied over the framework and teeth may be fabricated on the base. The prosthesis may be placed in the patient's mouth and connected to the abutments and/or implants which have been previously inserted into the patient's mouth weeks or months before.

Figure 14:
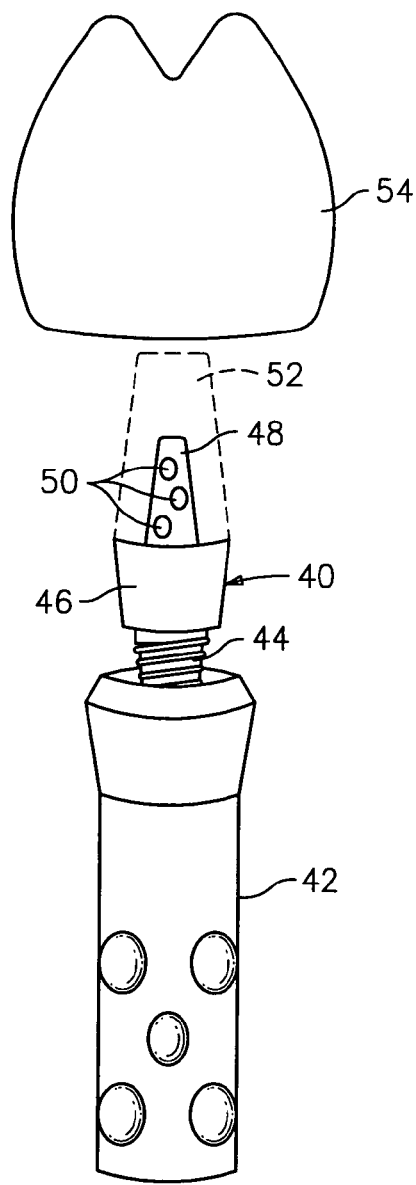
FIG. 14 is a perspective view of alternate embodiment of an implant system of the invention.

As set forth above, the implant system herein may be used for single crowns, small prostheses comprising one or a few teeth, or large or full arch prostheses comprising all or many teeth. The single implant crown system preferably includes an abutment or substructure bonded to a polymeric veneer material and a crown. The abutment or substructure preferably fits within the implant component which is implanted into the bone. The abutment or substructure may be fabricated of any known material such as metal, plastic, ceramic, polymeric material and mixtures thereof. FIG. 14 shows abutment 40 which fits in an implant 42. Abutment 40 includes a longitudinally extending lower end 44 which fits in implant 42 and collar 46 which may partially or fully fit within implant 42. Lower end 44 may be cemented and/or screwed into implant 42. Preferably, lower end 44 is threaded and can be screwed into implant 42. Abutment 40 also includes a longitudinally extending upper end 48 for placement of a crown thereon. Upper end 48 may include one or more holes 50 which assist in retaining a polymeric material 52. Holes 50 may be substituted with beads, nodules or the like for retaining a polymeric material. A crown or bridge retainer 54 may further be disposed on polymeric material 52. Polymeric material 52 may include any of the dental veneering materials in the art such as Sculpture® composite available from Jeneric/Pentron Inc., Wallingford, Conn., ArtGlass™ composite available from Heraeus Kulzer Inc., South Bend, Ind., and BelleGlass™ composite from Kerr, Orange, Calif.

Figure 15:
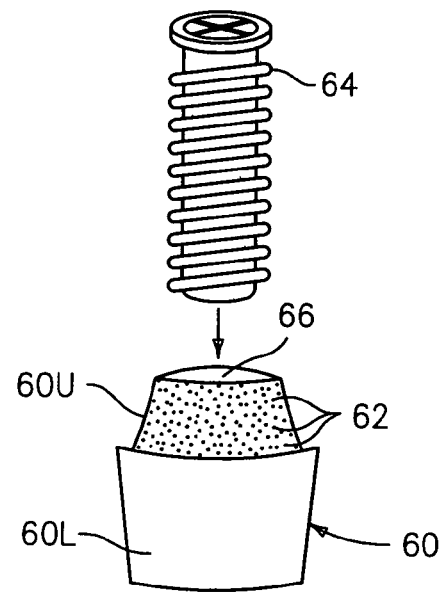
FIG. 15 is a perspective view of an alternate embodiment of the implant system of the invention.

FIG. 15 shows an alternative embodiment herein comprising an abutment or substructure 60 which fits into an implant. Abutment or substructure 60 may be comprised of metal, ceramic, plastic, polymeric or like material having sufficient strength to withstand the forces occurring in the mouth. Substructure 60 may comprise retentive beads 62 thereon to assist in the retention of a polymeric material. Beads 62 may be replaced with holes, nodules or the like for retaining polymeric material thereon. A screw 64 is inserted in opening or chimney 66 of substructure 60 to retain substructure 60 in an implant which has been placed in the mouth. Preferably lower section or collar 60L fits over an implant and upper section 60U is visible above the gingiva. Collar 60L may vary in height depending upon the size or depth of the opening in which it is inserted. Polymeric material such as Fibrekor® fiber reinforced composite and/or Sculpture® composite available from Jeneric/Pentron Inc., Wallingford, Conn. may be applied on upper section 60U indirectly outside the mouth to provide a prosthesis.

Fiber reinforced composite material 24 comprises a polymeric matrix and reinforcing fibers within the matrix. The fibers are embedded in the matrix manually or mechanically by a variety of techniques including, but not limited to matched die processes, autoclave molding, resin injection molding (RIM), sheet, dough and bulk molding, press molding, injection molding, reaction injection molding, resin transfer molding (RTM), compression molding, open molding, extrusion, pultrusion and filament winding. U.S. Pat. Nos. 4,717,341 and 4,894,012 to Goldberg et al. show methods of impregnation and are hereby incorporated by reference. Commercially available Fibrekor® fiber reinforced composite from Jeneric/Pentron Inc., Wallingford, Conn. may be used to build the fiber reinforced composite framework.

The polymeric matrix element of the composite is selected from those known in the art of dental materials, such as thermoset and thermoplastic materials, including but not being limited to polyamides, polyesters, polyolefins, polyimides, polyarylates, polyurethanes, vinyl esters or epoxy-based materials. Other polymeric matrices include styrenes, stryrene acrylonitriles, ABS polymers, polysulfones, polyacetals, polycarbonates, polyphenylene sulfides, and the like.

Preferred polymeric materials in the fiber reinforced composite include those based on acrylic and methacrylic monomers, for example those disclosed in U.S. Pat. Nos. 3,066,112, 3,179,623, and 3,194,784 to Bowen; U.S. Pat. Nos. 3,751,399 and 3,926,906 to Lee et al.; commonly assigned U.S. Pat. Nos. 5,276,068 and 5,444,104 to Waknine; and commonly assigned U.S. Pat. No. 5,684,103 to Jia et al., the pertinent portions of all which are herein incorporated by reference. An especially preferred methacrylate monomer is the condensation product of bisphenol A and glycidyl methacrylate, 2,2'-bis[4-(3-methacryloxy-2-hydroxy propoxy)-phenyl]-propane (hereinafter abbreviated "BIS-GMA"). Polyurethane dimethacrylates (hereinafter abbreviated "PUDMA"), triethylene glycol dimethacrylate (hereinafter abbreviated "TEGDMA"), polyethylene glycol dimethacrylate (hereinafter abbreviated "PEGDMA"), urethane dimethacrylate (hereinafter abbreviated "UDMA"), hexane diol dimethacrylate (hereinafter abbreviated "1,6 HDDMA") and polycarbonate dimethacrylate (hereinafter abbreviated "PCDMA") are also commonly-used principal polymers suitable for use in the present invention.

The polymeric matrix in the fiber reinforced composite typically includes polymerization initiators, polymerization accelerators, ultraviolet light absorbers, anti-oxidants, and other additives well known in the art. The polymeric matrices may be visible light curable, self-curing, dual curing, and vacuum, heat, and pressure curable compositions as well as any combination thereof. The visible light curable compositions include the usual polymerization initiators, polymerization accelerators, ultraviolet absorbers, fluorescent whitening agents, and the like. Preferred light curing initiators include camphorquinone (CQ) and trimethyl benzoyl phosphine oxide (TPO). The heat curable compositions, which are generally filled compositions, include, in addition to the monomeric components, a heat cure initiator such as benzoyl peroxide, 1,1'-azobis(cyclohexanecarbo-nitrile), or other free radical initiators. The preferred polymeric matrix is a curable matrix, wherein light cure effects partial cure of the matrix, and final curing is by heat under controlled atmosphere. Radiopaque agents may be included in the matrix The polymeric matrix in the fiber reinforced composite may further comprise at least one filler known in the art and used in dental restorative materials, the amount of such filler being determined by the specific use of the fiber-reinforced composite. Generally, the filler is added in an amount of up to about seventy percent by weight of the composite and preferably in an amount of up to about thirty percent by weight of the composite. Suitable fillers are those capable of being covalently bonded to the polymeric matrix itself or to a coupling agent that is covalently bonded to both. Examples of suitable filling materials include but are not limited to those known in the art such as silica, silicate glass, quartz, barium silicate, barium sulfate, barium molybdate, barium methacrylate, barium yttrium alkoxy ($Ba_2Y(OR)_x$), strontium silicate, barium borosilicate, strontium borosilicate, borosilicate, lithium silicate, amorphous silica, ammoniated or deammoniated calcium phosphate and alumina, zirconia, tin oxide, tantalum oxide, niobium oxide, and titania. Particularly suitable fillers for dental filling-type materials prepared in accordance with this invention are those having a particle size ranging from about 0.1-5.0 microns with a silicate colloid of 0.001 to about 0.07 microns and prepared by a series of milling steps comprising wet milling in an aqueous medium, surface etch milling and silanizing milling in a silane solution. Some of the aforementioned inorganic filling materials are disclosed in U.S. Pat. Nos. 4,544,359 and 4,547,531 to Waknine, the pertinent portions of which are incorporated herein by reference. Suitable organic filler materials are known in the art, including for example the poly(methacrylate) fillers described in U.S. Pat. No. 3,715,331 to Molnar. A mixture of organic and inorganic filler materials may also be used.

The reinforcing fiber element of the composite preferably comprises glass, carbon, graphite, polyaramid, polyethylene, or other fibers known in the art, such as polyesters, polyamides, and other natural and synthetic materials compatible with the polymeric matrix. Some of the aforementioned fibrous materials and fillers materials are disclosed in U.S. Pat. Nos. 4,717,341 and 4,894,012 both of which are incorporated herein by reference. The fibers may further be treated, for example, chemically or mechanically etched, silanized, or otherwise treated such as by grafting functional monomers to obtain proper coupling between the fibers and the resin matrix. Silanization renders the fibers hydrophobic, reducing the water sorption and improving the hydrolytic stability of the composite material, renders the fibers organophilic, improving wetting and mixing, and bonds the fibers to the polymeric matrix. Typical silane is A-174 (p-methacrylate propyl tri-methoxy silane), produced by OSI Specialties, NY.

The fibers preferably take the form of long, continuous filaments, although the filaments may be as short as 0.1 to 4 millimeters. Shorter fibers of uniform or random length might also be employed. Preferably, the fibers are at least partially aligned and oriented along the longitudinal dimensions of the strip. However, depending on the end use of the composite material, the fibers may also be otherwise oriented, including being normal or perpendicular to that dimension. The fibrous element may optionally take the form of a fabric. Fabric may be of the woven or non-woven type and is preferably preimpregnated with a polymeric material as set forth above. The fibrous component may be present in the fiber reinforced composite material in the range from about 20% to about 85% of the composite, and more preferably between about 30% to about 65% by weight.

The implant system may be sold in kit form in a variety of combinations including but not limited to cylinders, implants, composite material, abutments, screws, resin, superstructures and other materials necessary to fabricate implants.

While various descriptions of the present invention are described above, it should be understood that the various features can be used singly or in any combination thereof. Therefore, this invention is not to be limited to only the specifically preferred embodiments depicted herein.

Further, it should be understood that variations and modifications within the spirit and scope of the invention may occur to those skilled in the art to which the invention pertains. Accordingly, all expedient modifications readily attainable by one versed in the art from the disclosure set forth herein that are within the scope and spirit of the present invention are to be included as further embodiments of the present invention. The scope of the present invention is accordingly defined as set forth in the appended claims.

What is claimed is:

1. A framework for an implant system comprising:
one or more cylinders, wherein the one or more cylinders each comprise a substantially cylindrical body and one or more shelves disposed on a surface of the substantially cylindrical body, wherein the one or more shelves comprise one or more grooves having at least two sides; and fiber reinforced composite material retained on the one or more cylinders and wherein the fiber reinforced composite material is in the shape of bars.

2. An implant system comprising:
one or more abutments for connection to implants; and
a prosthesis comprising one or more cylinders for connection to the one or more abutments wherein each cylinder of the one or more cylinders comprises a substantially cylindrical body, one or more horizontally extending grooves having at least two sides, wherein the one or more horizontally extending grooves are disposed on a surface of the cylindrical body, and one or more vertically extending grooves having at least two sides, wherein the one or more vertically extending grooves are disposed on the surface of the cylindrical body; and
fiber reinforced composite material retained on the one or more cylinders.

3. The implant system of claim 2 further comprising implants.

4. The implant system of claim 2 wherein the fiber reinforced composite material is disposed in and between the one or more vertically extending grooves and is wrapped around the one or more cylinders.

5. An implant system comprising:
one or more abutments for connection to implants;
a prosthesis comprising one or more cylinders for connection to the one or more abutments wherein each cylinder of the one or more cylinders comprises a substantially cylindrical body, one or more horizontally extending grooves having at least two sides, wherein the one or more horizontally extending grooves are disposed on a surface of the cylindrical body, and one or more vertically extending grooves having at least two sides, wherein the one or more vertically extending grooves are disposed on the surface of the cylindrical body; and
a structural material disposed on the one or more cylinders.

6. The implant system of claim 5 further comprising implants.

7. The implant system of claim 5 wherein the structural material comprises fiber-reinforced composite material.

8. A method of making a prosthesis for an implant system comprising:
placing a series of cylinders onto a cast wherein each cylinder comprises a substantially cylindrical body, one or more horizontally extending grooves having at least two sides, wherein the one or more horizontally extending grooves are disposed on a surface of the cylindrical body, and one or more vertically extending grooves having at least two sides, wherein the one or more vertically extending grooves are disposed on the surface of the cylindrical body; and
building a structural framework on the series of cylinders.

9. The method of claim 8 wherein the structural framework comprises fiber reinforced composite material.

10. The method of claim 8 further comprising building teeth on the framework.

11. The method of claim 10 further comprising inserting the implant system into a patient's mouth.

12. An implant system comprising:
one or more abutments for connection to implants;
a prosthesis comprising one or more cylinders for connection to the one or more abutments wherein each cylinder of the one or more cylinders comprises a substantially cylindrical body and one or more grooves having at least two sides, wherein the one or more grooves are disposed on a surface of the substantially cylindrical body; and
fiber reinforced composite material retained on the one or more cylinders.

13. An implant system comprising:
one or more abutments for connection to implants;
a prosthesis comprising one or more cylinders for connection to the one or more abutments wherein each cylinder of the one or more cylinders comprises a substantially cylindrical body and one or more grooves having at least two sides, wherein the one or more grooves are disposed on a surface of the substantially cylindrical body; and
a structural material disposed on the one or more cylinders.

* * * * *